United States Patent [19]

Neumann

[11] Patent Number: 4,565,816

[45] Date of Patent: Jan. 21, 1986

[54] PIPERAZINE DERIVATIVES AND PHARMACEUTICAL COMPOSITION CONTAINING THEM

[75] Inventor: Peter Neumann, Berne, Switzerland

[73] Assignee: Sandoz Ltd., Basel, Switzerland

[21] Appl. No.: 498,952

[22] Filed: May 27, 1983

[30] Foreign Application Priority Data

| May 28, 1982 | [CH] | Switzerland | 3317/82 |
| Jun. 2, 1982 | [CH] | Switzerland | 3379/82 |
| Jul. 22, 1982 | [CH] | Switzerland | 4484/82 |
| Jul. 22, 1982 | [CH] | Switzerland | 4485/82 |

[51] Int. Cl.⁴ .................. A61K 31/495; C07D 401/14
[52] U.S. Cl. .................................... 514/253; 544/345; 544/350; 544/361; 544/362; 544/398; 544/399; 544/403; 260/244.4
[58] Field of Search .................. 544/362; 424/251; 514/253; 260/244.4

[56] References Cited

U.S. PATENT DOCUMENTS 3,435,036  3/1969  Regnier et al. .................... 544/362

OTHER PUBLICATIONS

Derwent Abstract No. 44369R.
Derwent Abstract No. 16864V.
Derwent Abstract No. 42579A.
Derwent Abstract No. 82662B.
Naunyn–Schmiedeberg's Archives of Pharm., Suppl. to vol. 316 (1981).
Derwent Abstract No. 24377E.

*Primary Examiner*—Glennon H. Hollrah
*Assistant Examiner*—James H. Turnipseed
*Attorney, Agent, or Firm*—Gerald D. Sharkin; Robert S. Honor; Joseph J. Borovian

[57] ABSTRACT

Piperazine derivatives or pharmaceutically acceptable acid addition salts thereof are useful as neuroleptic, anti-hypertensive or bradycardic agents.

6 Claims, No Drawings

PIPERAZINE DERIVATIVES AND PHARMACEUTICAL COMPOSITION CONTAINING THEM

The present invention relates to piperazine derivatives, their production and pharmaceutical compositions containing them.

According to the present invention there are provided compounds of formula I,

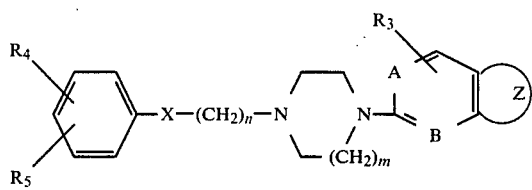

wherein one of A and B is N and the other CH, Z is a ring sharing two ring carbon atoms with the ring containing A and B and having the formula II or III,

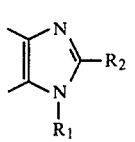 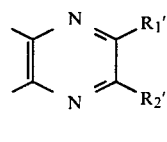

II                III $R_1$ and $R_2$ are each, independently, hydrogen, $(C_{1-6})$alkyl or $(C_{7-10})$phenylalkyl, optionally monosubstituted in the phenyl ring by halogen, $(C_{1-4})$alkyl or $(C_{1-4})$alkoxy, $R_3$ is hydrogen or $(C_{1-4})$alkyl, $R_1'$ and $R_2'$ signify hydrogen or $(C_{1-4})$alkyl, or $R_1'$ and $R_2'$ together signify trimethylene, tetramethylene or pentamethylene, m is 1 or 2, $R_4$ and $R_5$ are each, independently, hydrogen, halogen, $(C_{1-4})$alkyl, $(C_{1-4})$alkoxy, $(C_{2-4})$acyl or trifluoromethyl, and X is —CH$_2$— and n is 0, 1, 2 or 3, or X is —CO— and n is 1, 2 or 3, or X is —O— and n is 2 or 3, and acid addition salts thereof.

In formula I $R_3$ is attached to a ring carbon atom. Halogen means fluorine, chlorine, bromine or iodine, preferably fluorine or chlorine.

Most suitably $R_4$ is para to the X moiety. $R_4$ is preferably halogen, especially fluorine. $R_5$ is preferably hydrogen or halogen. Suitably X is —O— but more suitably X is —CO—. Particularly suitable values for n are 2 or 3 preferably 3. A preferred value for m is 1. $R_1'$ and $R_2'$ are preferably the same.

The present invention also provides a process for the production of a compound of formula I, which comprises (a) producing a compound of formula Ia,

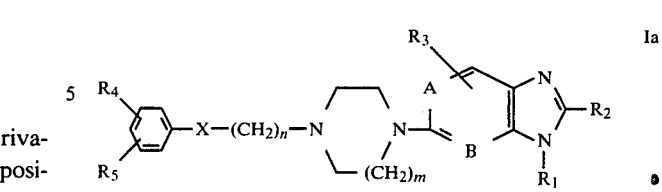

wherein A, B, $R_1$–$R_5$, X, m and n are as defined above, by reacting a compound of formula IV,

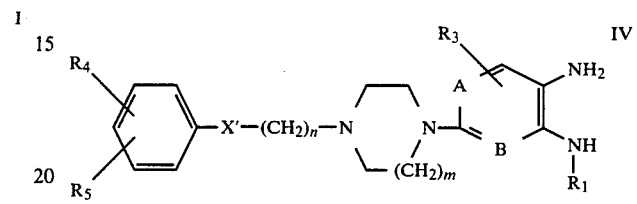

wherein A, B, $R_1$, $R_3$–$R_5$, m and n are as defined above, and X' has the same significance as X, whereby if desired the carbonyl group is protected, with a compound of formula V,

wherein $R_2$ is as defined above, and either (i) Y and Z together with the carbon atom to which they are bound are >C=O and U is a leaving group, or (ii) Y, Z and U are leaving groups, or (b) producing a compound of formula Ib,

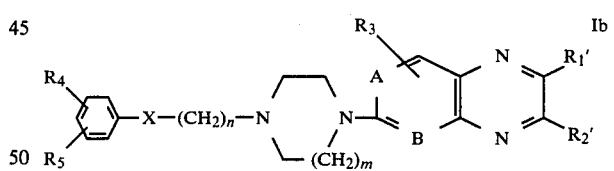

wherein A, B, $R_1'$, $R_2'$, $R_3$–$R_5$, X, m and n are as defined above, by reacting a compound of formula IV wherein $R_1$ is hydrogen, with a compound of formula VI,

wherein $R_1'$ and $R_2'$ are as defined above, and subsequently removing any carbonyl-protecting group present.

Compounds of formula Ia wherein $R_1$ is hydrogen, may exist in a tautomeric form of formula Ia',

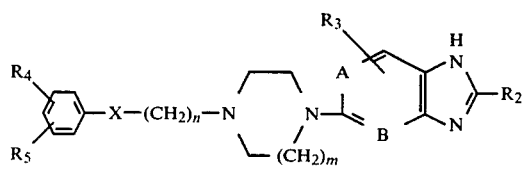

Such tautomeric forms are also encompassed in the present compounds of formula I.

Process (a) may be effected in conventional manner for analogous ring closure reactions e.g. by condensation. A suitable reaction temperature is 40° to 200°, preferably 80° to 140°. The reaction may, if desired, also be carried out in the presence of an inert organic solvent. Suitable solvents include tetrahydrofuran, dioxan, methylethylketone, dimethylsulfoxide, n-propanol, toluene or N-methylpyrrolidone. An excess of a compound of formula V may be employed to provide the reaction medium. In the compounds of formula V U is e.g. halogen, especially chlorine or bromine, hydroxy, ($C_{1-4}$)alkoxy, amino, di($C_{1-4}$)alkylamino or —O—CO—$R_2$. The reaction is conveniently carried out in the presence of an acid, such as hydrochloric acid or polyphosphoric acid, when Y and Z together with the carbon atom to which they are bound are >C=O and U is hydroxy, ($C_{1-4}$)alkoxy, amino or di($C_{1-4}$)alkylamino. When Y, X and Z are leaving groups then they are preferably ($C_{1-4}$)alkoxy.

Compounds of formula Ia may also be obtained by cyclising a compound of formula VII,

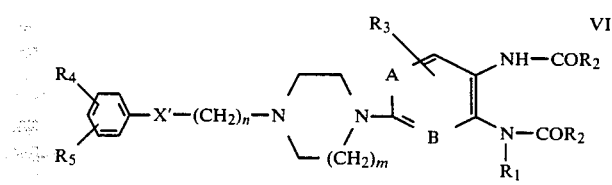

wherein A, B, $R_1$–$R_5$, X', m and n are as defined above. The cyclisation may be effected at temperatures between 60° to 230°, preferably 100° to 150°. The reaction may be performed in the presence or absence of a solvent. Suitable solvents include dioxane, dimethylsulfoxide, n-propanol, toluene or N-methylpyrrolidone.

Conveniently an acid such as hydrochloric or polyphosphoric acid is present. The cyclisation may also be effected without an acid.

Process (b) may be effected in conventional manner for analogous ring condensations. The process is conveniently carried out at a temperature in the range from 40° to 160°, preferably 60° and 120°. Suitable solvents include methanol, tetrahydrofuran, dioxan, toluene or n-propanol.

Where X is —CO— in the resulting compound of formula I, it may be convenient to use a carbonyl-protecting group, e.g. a dialkylketal group such as dimethyl or diethyl ketal group, or a alkylene ketal group such as ethylene or n-propylene ketal group. The removal of such group can be effected in known manner.

Compounds of formula IV may, for example, be obtained via the following reaction scheme:

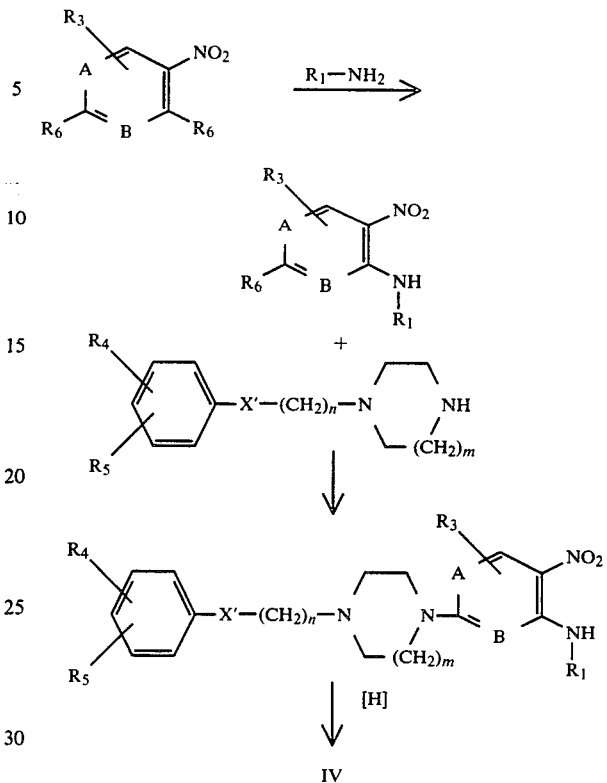

$R_6$ = bromine or especially chlorine

Any carbonyl-protecting group can be removed in known manner either before condensation with a compound of formula V or VI or afterwards.

Compounds of formula VII may be obtained by reacting a compound of formula IV with a compound of formula V. The reaction is conveniently carried out in presence of an acid binding agent such as triethylamine or pyridine. Suitable temperatures may be from 0° to 60°, preferably 20° to 40°. The reaction may be effected in absence or presence of an inert organic solvent. Suitable solvents include toluene, n-propanol, dioxan or N-methylpyrrolidone. The resulting compounds of formula VII can be cyclised in situ to compounds of forumula Ia by suitable regulation of the reaction temperature.

The reaction may be followed by conventional means, e.g. thin layer chromatography to determine when satisfactory yields of a compound of formula VII or Ia are obtained.

Insofar as the production of starting materials is not particularly described these compounds are known or may be produced in analogous manner to known compounds or to processes described herein.

The compounds of formula VII, wherein A, B, $R_1$–$R_5$, m and n are as defined above and X' is —$CH_2$—, —CO— or —O— are of particular interest.

The compounds of formulae I and VII may be converted into acid addition salts thereof in conventional manner and vice versa. Suitable acids include for example, hydrochloric acid, hydrobromic acid, succinic acid, maleic acid or fumaric acid.

In the following examples all temperatures are given in degrees Centigrade and are uncorrected.

In the Tables the following abbreviations are used:

(2) bis-maleate
(3) hydrochloride
(4) dihydrochloride
(5) decomposition

EXAMPLE 1

1-(4-Fluorophenyl)-4-[4-(1H-imidazo[4,5-b]pyridin-5-yl)-1-piperazinyl]-1-butanone [compound Ia]

9 g 1-(4-Fluorophenyl)-4-[4-(2,3-diamino-pyridin-6-yl)-1-piperazinyl]-1-butanone and 60 ml (98%) formic acid are boiled for 5 hours. The mixture is diluted with 80 ml water and made alkaline at room temperature with conc. sodium hydroxide solution. The precipitate is filtered off, washed with water, dried and dissolved in hot ethyl acetate. The hot solution is treated with active carbon and filtered. The title compound is precipitated on cooling, m.p. 166°–167°.

Purification may be effected by chromatography on silica-gel with acetone as eluant.

The starting material may be obtained as follows:

6 g 2-amino-6-chloro-3-nitropyridine, 12.6 g 1-(4-fluorophenyl)-4-(1-piperazinyl)-1-butanone dihydrochloride and 20 g potassium carbonate in 120 ml n-propanol are stirred under reflux for 2½ hours. The mixture is then treated with 400 ml water, stirred for further 10 minutes and cooled in ice bath. The resulting precipitate is filtered off, washed with water, dissolved in methylene chloride, dried over sodium sulphate and evaporated. The resulting 1-(4-fluorophenyl)-4-[4-(2-amino-3-nitro-pyridin-6-yl)-1-piperazinyl]-1-butanone, m.p. 128°–130°, is without further purification dissolved in 400 ml methanol. 3 g palladium on charcoal (5%) are added to the solution and the mixture is hydrogenated under normal conditions. The catalyst is filtered off and the solvent distilled off to give 1-(4-fluorophenyl)-4-[4-(2,3-diaminopyridin-6-yl)-1-piperazinyl]-1-butanone which is used without further purification.

EXAMPLE 2

1-(4-Fluorophenyl)-4-[4-(1Hazinyl]-1-butanone idin-5-yl)-1-piper[compound Ia]

7.5 g 1-(4-Fluorophenyl)-4-[4-(2,3-diamino-pyridin-6-yl)-1-piperazinyl]-1-butanone ethylene ketal and 50 ml (99%) formic acid are refluxed for 5 hours. The formic acid is then distilled off. The residue is diluted with the 2 fold amount of water and made alkaline with conc. sodium hydroxide solution. The resulting precipitate is filtered off, washed with water and taken up with 80 ml hot acetone. The solution is filtered, and cooled. The precipitate is filtered off and recristallised from ethyl acetate using active charcoal to give the title compound, m.p. 167°–168°.

The starting material may be obtained as follows:

(a)

1-(4-Fluorophenyl)-4-[4-(2-amino-3-nitro-pyridin-6-yl)-1-piperazinyl]-1-butanone ethylene ketal 5.6 g 2-amino-6-chloro-3-nitropyridine, 10 g 1-(3-[2-(4-fluorophenyl)-1,3-dioxolan-2-yl]-propyl)piperazine, 5 g potassium carbonate and 100 ml n-propanol are refluxed 2½ hours. After cooling the precipitate is filtered off. The filtrate is concentrated to ca. 10 ml and diluted with the same volume of diisopropyl ether. The resulting cristallisate is admixed with the above mentioned precipitate and partitioned between water and methylene chloride. The organic phase is filtered and evaporated to give the heading compound, m.p. 117°–118°.

(b)

1-(4-Fluorophenyl)-4-[4-(2,3-diamino-pyridin-6-yl)-1-piperazinyl]-butanone ethylene ketal 12 g of the example (a) compound are dissolved with heating in 1200 ml methanol. After addition of 1 g palladium on charcoal (5%) the mixture is hydrogenated under normal conditiions. The catalyst is filtered off and the solution is evaporated to give the heading compound, which can be used without further purification. M.p. 118°–119° (recrystallised from ethyl acetate/diisopropyl ether).

EXAMPLE 3

In analogous manner to that disclosed in Example 1 the following compounds of formula Ia are produced wherein m is 1 and $R_3$ is hydrogen via the corresponding compounds of formula VII:

| Example | A | B | $R_1$ | $R_2$ | n | X | $R_4$ | $R_5$ | m.p. |
|---|---|---|---|---|---|---|---|---|---|
| a | CH | N | $CH_3$ | H | 0 | $CH_2$ | H | H | 114–115 |
| b | CH | N | $CH_3$ | H | 3 | CO | 4-F | H | 118–119 |
| c | CH | N | H | $CH_3$ | 3 | CO | 4-F | H | 176–178 |
| d | CH | N | $CH_3$ | $CH_3$ | 3 | CO | 4-F | H | 152–154 |
| e | CH | N | $CH(CH_3)_2$ | H | 3 | CO | 4-F | H | 97–98 |
| f | CH | N | $CH_2C_6H_5$ | H | 3 | CO | 4-F | H | 110–112 |
| g | CH | N | $CH_3$ | H | 1 | $CH_2$ | H | H | 124–126 |
| h | CH | N | H | H | 3 | O | 4-F | H | 150–153 |
| i | CH | N | H | $C_2H_5$ | 3 | CO | 4-F | H | 152–153 |
| j | .CH | N | H | $n-C_3H_7$ | 3 | CO | 4-F | H | >228[(4)(5)] |
| k | CH | N | H | $CH(CH_3)_2$ | 3 | CO | 4-F | H | 240–250[(3)(5)] |
| l | CH | N | $CH_3$ | $n-C_3H_7$ | 3 | CO | 4-F | H | 131–133 |
| m | CH | N | $CH_3$ | $CH(CH_3)_2$ | 3 | CO | 4-F | H | 128–129 |
| n | CH | N | H | $CH_2C_6H_5$ | 3 | CO | 4-F | H | |
| o | CH | N | H | $CH_3$ | 3 | O | 4-F | H | 186–190 |
| p | CH | N | H | $C(CH_3)_3$ | 3 | CO | 4-F | H | |
| q | CH | N | $C_2H_5$ | H | 3 | CO | 4-F | H | 85–87 |
| qq | CH | N | $CH_3$ | $C_2H_5$ | 3 | CO | 4-F | H | 134–135 |
| r | N | CH | H | H | 3 | CO | 4-F | H | 184–185 |
| s | N | CH | H | $CH_3$ | 3 | CO | 4-F | H | 180–183 |
| t | N | CH | H | H | 3 | O | 4-F | H | 182–183.5 163–164.5[(2)(5)] |
| u | N | CH | H | $C_2H_5$ | 3 | CO | 4-F | H | 201–205 |
| v | N | CH | H | $CH(CH_3)_2$ | 3 | CO | 4-F | H | 195–197 |
| w | N | CH | $CH_3$ | $CH_3$ | 3 | CO | 4-F | H | 188–190 |
| x | N | CH | $CH_3$ | H | 3 | CO | 4-F | H | 177.5–178.5 |
| y | N | CH | $CH(CH_3)_2$ | H | 3 | CO | 4-F | H | |

-continued

| Example | A | B | $R_1$ | $R_2$ | n | X | $R_4$ | $R_5$ | m.p. |
|---|---|---|---|---|---|---|---|---|---|
| z | N | CH | H | $CH_2C_6H_5$ | 3 | CO | 4-F | H | 225–240[4][5] |
| vv | N | CH | H | $CH_3$ | 3 | O | 4-F | H | |

EXAMPLE 4

4-[4-(4,5-Diacetylamino-2-pyridinyl)-1-piperazinyl]-1-(4-fluorophenyl)-1-butanone [compound VII]

8.3 g 1-(4-Fluorophenyl)-4-[4-(4,5-diamino-pyridin-2-yl)-1-piperazinyl]-1-butanone are stirred for 20 hours with 4.5 ml acetyl chloride, 9 ml triethylamine and 150 ml toluene at room temperature. The precipitate is filtered off and dissolved in 2N HCl. The solution is treated with active charcoal, filtered and made alkaline with aqueous $NH_3$. The resulting precipitate is washed with a little volume of ether and ethanol and is recrystallized from ethanol to give the title compound, m.p. 206°–209°. (dried in high vacuo above 120°).

The starting material may be prepared as described in Example 1 starting from 4-amino-2-chloro-5-nitro-pyridine via 1-(4-fluorophenyl)-4-[4-(4-amino-5-nitro-pyridin-2-yl)-1-piperazinyl]-1-butanone to give 1-(4-fluorophenyl)-4-[4-(4,5-diamino-pyridin-2-yl)-1-piperazinyl]-1-butanone, m.p. 166°–169° (from ethyl acetate).

EXAMPLE 5

In analogous manner to that disclosed in Example 4 the following compounds of formula VII are produced wherein m is 1 and $R_3$ is hydrogen:

| Example | A | B | $R_1$ | $R_2$ | n | X | $R_4$ | $R_5$ | m.p. |
|---|---|---|---|---|---|---|---|---|---|
| a | CH | N | $CH_3$ | H | 0 | $CH_2$ | H | H | |
| b | CH | N | $CH_3$ | H | 3 | CO | 4-F | H | |
| c | CH | N | H | $CH_3$ | 3 | CO | 4-F | H | 124–127 |
| d | CH | N | $CH_3$ | $CH_3$ | 3 | CO | 4-F | H | 179 |
| e | CH | N | $CH(CH_3)_2$ | H | 3 | CO | 4-F | H | |
| f | CH | N | $CH_2C_6H_5$ | H | 3 | CO | 4-F | H | |
| g | CH | N | $CH_3$ | H | 1 | $CH_2$ | H | H | |
| h | CH | N | H | H | 3 | O | 4-F | H | |
| i | CH | N | H | $C_2H_5$ | 3 | CO | 4-F | H | 112–114 |
| j | CH | N | H | $n$-$C_3H_7$ | 3 | CO | 4-F | H | |
| k | CH | N | H | $CH(CH_3)_2$ | 3 | CO | 4-F | H | 133–136 |
| l | CH | N | $CH_3$ | $n$-$C_3H_7$ | 3 | CO | 4-F | H | |
| m | CH | N | $CH_3$ | $CH(CH_3)_2$ | 3 | CO | 4-F | H | |
| n | CH | N | H | $CH_2C_6H_5$ | 3 | CO | 4-F | H | |
| o | CH | N | H | $CH_3$ | 3 | CO | 4-F | H | |
| p | CH | N | H | $C(CH_3)_3$ | 3 | CO | 4-F | H | |
| q | CH | N | $C_2H_5$ | H | 3 | CO | 4-F | H | |
| r | N | CH | H | H | 3 | CO | 4-F | H | 155–157 |
| s | N | CH | H | $CH_3$ | 3 | O | 4-F | H | 178–179.5 |
| t | N | CH | H | H | 3 | O | 4-F | H | |
| u | N | CH | H | $C_2H_5$ | 3 | CO | 4-F | H | 183–185 |
| v | N | CH | H | $CH(CH_3)_2$ | 3 | CO | 4-F | H | |
| w | N | CH | $CH_3$ | $CH_3$ | 3 | CO | 4-F | H | 192–193 |
| x | N | CH | $CH_3$ | H | 3 | CO | 4-F | H | |
| y | N | CH | $CH(CH_3)_2$ | H | 3 | CO | 4-F | H | |
| z | N | CH | H | $CH_2C_6H_5$ | 3 | CO | 4-F | H | |

EXAMPLE 6

1-(4-Fluorophenyl)-4-[4-(2-methyl-1H-imidazo[4,5-c]pyridin-6-yl)-1-piperazinyl]-1-butanone (compound Ia from compound of formula VII)

5 g 4-[4-(4,5-Diacetylamino-2-pyridinyl)-1-piperazinyl]-1-(4-fluorophenyl)-1-butanone and 25 g polyphosphoric acid are stirred and heated 1 hour at 140°. The reaction mixture is then cooled to room temperature, treated with 200 ml water, made alkaline with aqueous NaOH solution and extracted with methylene chloride. The extract is dried and evaporated. The residue is recrystallized from dichlormethane/diisopropylether to give the title compound, m.p. 180°–183°. M.p. of the bis-maleate 172°–173.5°.

EXAMPLE 7

4-[4-(2,3-Dimethyl-pyrido[2,3-b]pyrazin-6-yl)-1-piperazinyl]-1-(4-fluorophenyl)-1-butanone (compound Ib)

9 g 4-[4-(2,3-Diamino-pyridin-6-yl)-1-piperazinyl]-1-(4-fluorophenyl)-1-butanone and 2.6 g butane-2,3-dione in 250 ml methanol are stirred under reflux for 1 hour. The solvent is evaporated. The residue is dissolved in hot ethyl acetate and treated with active charcoal, filtered and cooled to give the title compound, m.p. 155°–156°.

EXAMPLE 8

In analogous manner to that disclosed in Example 7 the following compounds of formula Ib are produced wherein m is 1 and $R_3$ is hydrogen:

| Example | A | B | $R_1'$ | $R_2'$ | n | X | $R_4$ | $R_5$ | m.p. |
|---|---|---|---|---|---|---|---|---|---|
| a | CH | N | H | H | 3 | CO | 4-F | H | 130–131 |
| b | CH | N | $C_2H_5$ | $C_2H_5$ | 3 | CO | 4-F | H | 99–100 |
| c | N | CH | $CH_3$ | $CH_3$ | 3 | CO | 4-F | H | 138–139 |
| d | N | CH | H | H | 3 | CO | 4-F | H | 124–126 |
| e | N | CH | $C_2H_5$ | $C_2H_5$ | 3 | CO | 4-F | H | 118–121 |
| f | N | CH | —$(CH_2)_4$— | | 3 | CO | 4-F | H | 138–140 |
| g | N | CH | H | H | 3 | O | 4-F | H | 98– |

EXAMPLE 9

In analogous manner to that disclosed in Example 1 the following compounds of formula Ia may be prepared:

| Ex. | A | B | R₁ | R₂ | R₃ | m | n | X | R₄ | R₅ |
|---|---|---|---|---|---|---|---|---|---|---|
| a | CH | N | (CH₂)₂—[phenyl-OCH(CH₃)₂] | H | 7-nC₃H₇ | 1 | 3 | CH₂ | 3-Cl | 5-Cl |
| b | CH | N | H | (CH₂)₃—[phenyl-Cl] | 6-nC₄H₉ | 1 | 1 | CH₂ | 3-OC₂H₅ | 5-OC₂H₅ |
| c | N | CH | C₂H₅ | CH₂—[phenyl-C(CH₃)₃] | 4-CH₃ | 2 | 3 | O | 3-COC₂H₅ | H |

EXAMPLE 10

In analogous manner to that disclosed in Example 7 the following compounds of formula Ib may be prepared:

| Example | A | B | R₁' | R₂' | R₃ | m | n | X | R₄ | R₅ |
|---|---|---|---|---|---|---|---|---|---|---|
| a | CH | N | H | H | 8-C₂H₅ | 1 | 2 | O | 3-Cl | 5-Cl |
| b | CH | N | —(CH₂)₃— |  | H | 2 | 3 | CH₂ | 3-CF₃ | H |
| c | N | CH | C₂H₅ | C₂H₅ | 5-CH₃ | 1 | 2 | CH₂ | 2-OCH₃ | H |

EXAMPLE 11

In analogous manner to that disclosed in Example 4 the following compounds of formula VII may be prepared:

| Ex. | A | B | R₁ | R₂ | R₃ | m | n | X | R₄ | R₅ |
|---|---|---|---|---|---|---|---|---|---|---|
| a | CH | N | (CH₂)₂—[phenyl-OCH(CH₃)₂] | H | 4-nC₃H₇ | 1 | 3 | CH₂ | 3-Cl | 5-Cl |
| b | CH | N | H | (CH₂)₃—[phenyl-Cl] | 5-nC₄H₉ | 1 | 1 | CH₂ | 3-OC₂H₅ | 5-OC₂H₅ |
| c | N | CH | C₂H₅ | CH₂—[phenyl-C(CH₃)₃] | 2-CH₃ | 2 | 3 | O | 3-COC₂H₅ | H |

The compounds of formulae I and VII are useful because they possess pharmacological activity in animals and are therefore useful as pharmaceuticals, e.g. for therapy. In particular, the compounds of formulae I and VII are useful as neuroleptic agents in the treatment of e.g. psychotic disorders such as schizophrenia, as indicated in standard tests, e.g. by an inhibition of locomotion in mice. In this test groups of 3 male mice (18–24 g, OF-1, Sandoz Basle) received 3.2, 10, 32, 100 and 320 mg p.o. of the test drug. 1 hour after drug administration the mice were observed individually and their locomotion compared with that of control. The locomotion of the animals was observed and the ED$_{min}$ (the minimum dose at which significant inhibition was observed) determined.

The compounds of formulae I and VII bind further on $^3$H-Spiperone binding sites in the brain [modified method of J. Leysen et al., Biochem. Pharmac. 27, 307 (1978)]. The test was performed as follows: fresh calf brain striatal tissue was homogenized in the 25 fold volume of Tris buffer (pH 7.4, 50 mM, 120 mM sodium chloride) and centrifuged. The pellets were suspended in the 22 fold volume of Tris buffer, incubated for 15 minutes at 37° C. and centrifuged. The pellets were suspended in the 300 fold volume of Tris buffer. The composition of the assay mixtures was as follows: 45 mM Tris buffer pH 7.7, 108 mM sodium chloride, membranes corresponding to 6 mg of original tissue weight, 0.1 nM $^3$H-Spiperone, $5 \times 10^{-7}$M Cinanserin to eliminate the contribution of 5-HT$_2$ receptors and 1 $\mu$M unlabelled Spiperone for the determination of non-specific binding. To determine the inhibition of the specific binding of $^3$H-Spiperone the test drugs were added to give 5 to 9 different concentrations between 1 nM and 10 $\mu$M, each in duplicate. After incubation for 40 minutes at room temperature, the assay mixtures were raidly filtered through Whatman GF/B filter, the filters washed twice with 5 ml of ice cold Tris buffer and scintillation-counted. The IC$_{50}$ values (concentration of a test drug which inhibits specific binding of $^3$H-Spiperone by 50%) are determined by linear regression analysis. Values for representative compounds in the above tests are given below:

| Example | Locomotor inhibition ED$_{min}$ mg/kg p.o. | Receptor binding IC$_{50}$ nM $^3$H—Spiperone |
|---|---|---|
| 1 | 1 | 306 |
| 3r | ≦3.2 | 441 |
| 5c | 1 | 4600 |
| 7 | 10 | 205 |
| 8c | 10 | 121 |
| 3i | 3.2 | 246 |
| Clozapine | 3.2 | 990 |

For the above mentioned use the dosage will, of course, vary depending on the compound employed, mode of administration and therapy desired. However, in general, satisfactory results are obtained with a daily dosage of from about 0.1 mg to about 100 mg per kg animal body weight, conveniently given in divided doses 2 to 4 times a day or in sustained release form. For the larger mammals, the total daily dosage is in the range from about 25 mg to about 600 mg, and dosage forms suitable for oral administration comprise from about 6 mg to about 300 mg of the compounds admixed with a solid or liquid pharmaceutical carrier or diluent.

The compounds of formulae I and VII are furthermore useful as anti-hypertensive agents, as indicated in standard tests, for example in the $^3$H-Prazosin binding assay for α$_1$-receptors [modified method of Greengrass P., et al., Eur. J. Pharmac. 55, 323-326 (1979)]. The test was performed as follows:

Fresh calf brain cortex tissue is homogenized in a 20 fold volume of Tris-HCl buffer (50 mM, pH 7.7), using a Polytron PT 20, and centrifuged at 30'000 xg for 25 min. The pellets are resuspended in a 13 fold volume of the same buffer, incubated for 15 min at 37° C., and recentrifuged at 50'000 xg for 11 min. The pellets of this centrifugation are frozen at −20° C. and resuspended in a 60 fold volume of the same buffer as above before use for the binding experiment. The composition of the assay mixtures (total volume=2 ml) is as follows: 50 mM Tris-HCl pH 7.7, membranes corresponding to 30 mg of original tissue weight, and 0.3 nM $^3$H-Prazosin. The assays for the definition of nonspecific binding additionally contain phentolamine at a concentration of 10 $\mu$M. To assess the potency of drugs in inhibiting specific $^3$H-Prazosin binding (difference between total and nonspecific binding), the test compounds are added to give 5 to 9 different concentrations between 1 nM and 10 $\mu$M, each in duplicate. After incubation for 40 min at room temperature, the assay mixtures are rapidly filtered through Whatman GF/B filters and washed twice with 5 ml of ice cold Tris buffer. The radioactivity of the filters is estimated by scintillation counting. For example the IC$_{50}$ of the Example 4 compound is <1 nM, of the Example 3d compound is 2.2 nM and of Guanfacine 3700 nM.

In another test female normotonic rats (200–350 g, Sprague-Dawley, Süddeutsche Tierfarm, Tuttlingen, FRG) were anaesthetized with urethane (1.5–1.75 g/kg i.p. in 2 portions) and a tracheal cannula was inserted. Blood pressure and heart rate were recorded from the carotid artery by conventional methods. Test drug were administered by the jugular or the femoral vein. Body temperature was maintained at 37° C. by means of a temperature regulator (Alfos MK-4) triggered by a thermistor on the animal. After adaptation, increasing doses of the test drug were injected i.v. to give the following cumulative doses: 3, 13, 43, 143, 343 and 1443 $\mu$g/kg. ED 75% is the dose required to reduce the blood pressure on the heart rate to 75% of pretreatment values. It was obtained through interpolation. The ED$_{75}$ of the Example 4 compound is 6 $\mu$g, of Example 5s compound 3 $\mu$g, of Example 8 g 4 $\mu$g and of Guanfacine 57 $\mu$g.

For this use the dosage will, of course, vary depending on the compound employed, mode of administration and condition to be treated. However, in general, satisfactory results are obtained with a daily dosage of from about 0.01 to about 30 mg per kg animal body weight, conveniently given in divided doses 2 to 4 times a day, or in sustained release form. For the larger mammals the total daily dosage is in the range from about 5 to about 100 mg and dosage forms suitable for oral administration comprise from about 1 to about 50 mg of the compound admixed with a solid or liquid pharmaceutical carrier or diluent.

The compounds of formulae I and VII possess further bradycardiac activity, as indicated in standard tests. For example, in guinea-pig atria in vitro [method of R. P. Hof and G. Scholtysik, J. of Cardiovascular Pharmacology 5, 176–183 (1983)] a decrease of the heart rate of spontaneously beating atria is observed at a bath concentration of from about 1 $\mu$M to about 100 $\mu$M. The concentration decreasing the rate of the spontaneously beating atria by 25% (EC$_{25}$ values) for some compounds of the present invention and the standard Alinidin are given in the following Table:

| Compound | EC$_{25}$ $\mu$M |
|---|---|
| 1 | 7.8 |
| 8d | 4.0 |
| 8g | 2.15 |
| Alinidin | 6.5 |

The compounds of formulae I and VII are therefore useful as bradycardic agents, e.g. for the prophylaxis and treatment of cardiac disorders such as Angina pectoris or heart rhythm disturbances such as sinus tachycardia.

For this use the dosage will, of course, vary depending on the compounds employed, mode of administration and therapy desired. However, in general, satisfactory results are obtained with a daily dosage of from about 0.05 mg to about 2 mg per kg animal body weight, conveniently given in divided doses 2 to 4 times a day or in sustained release form. For the larger mammals, the total daily dosage is in the range from about 10 mg to about 100 mg, and dosage forms suitable for oral administration comprise from about 2 mg to about 50 mg of the compounds admixed with a solid or liquid pharmaceutical carrier or diluent.

The compounds of formulae I and VII may be administered in similar manner to known standards for use in the above-mentioned utilities, for example, for the neuroleptic activity, Clozapine. The suitable daily dosage for a particular compound will depend on a number of factors such as its relative potency of activity. It has for example been determined that the preferred compounds of this invention, the Example 1 and Example 3i compounds, produce stronger effects in the $^3$H-Spiperone binding test than Clozapine. This indicates that the compounds of Examples 1 and 3i may be administered at similar or lower dosages to that of Clozapine for the neuroleptic indication.

For the neuroleptic use the daily oral dosage for the compound of Example 1 and 3i is indicated to be from 50 to 600 mg.

The compounds of formulae I and VII may be administered in pharmaceutically acceptable acid addition salt form. Such acid addition salts exhibit the same order of activity as the free base forms. The present invention also provides a pharmaceutical composition comprising a compound of formulae I or VII or a pharmaceutical acceptable acid addition salt thereof, in association with a pharmaceutical carrier or diluent. Such compositions may be in the form of, for example, a solution or a tablet.

The neuroleptic activity is the preferred indication for the compounds of formula I. In this indication the preferred compounds are the Example 1 and 3i compounds.

The bradycardiac activity is the preferred indication for the compounds of formula VII. Preferred in this indication is the compound of Example 8g.

In one group of compounds of formula I A is CH, B is N, Z is a ring of formula II, $R_1$, $R_2$ and $R_3$ are each, independently, hydrogen or $(C_{1-4})$alkyl, m is 1, $R_4$ and $R_5$ are each, independently, hydrogen, halogen, $(C_{1-4})$alkyl, $(C_{1-4})$alkoxy, $(C_{2-4})$acyl or trifluoromethyl and X is —CH$_2$— and n is 0, 1, 2 or 3, or X is —CO— and n is 1, 2 or 3, or X is —O— and n is 2 or 3, and acid addition salts thereof.

In another group of compounds of formula I A is N, B is CH, Z is a ring of formula II, $R_1$, $R_2$ and $R_3$ are each, independently, hydrogen or $(C_{1-4})$alkyl, m is 1, $R_4$ and $R_5$ are each, independently, hydrogen, halogen, $(C_{1-4})$alkyl, $(C_{1-4})$alkoxy, $(C_{2-4})$acyl or trifluoromethyl and X is —CH$_2$— and n is 0, 1, 2 or 3, or X is —CO— and n is 1, 2 or 3, or X is —O— and n is 2 or 3, and acid addition salts thereof.

Another group of compounds comprises compounds of formula I wherein A is CH, B is N, Z is a ring of formula III, $R_1'$, $R_2'$ and $R_3$ are each independently, hydrogen or $(C_{1-4})$ alkyl, m is 1, $R_4$ and $R_5$ are each, independently, hydrogen, halogen, $(C_{1-4})$alkyl, $(C_{1-4})$alkoxy, $(C_{2-4})$acyl or trifluoromethyl and X is —CH$_2$— and n is 0, 1, 2 or 3, or X is —CO— and n is 1, 2 or 3, or X is —O— and n is 2 or 3, and acid addition salts thereof.

In another group of compounds of formula I A is N, B is CH, Z is a ring of formula III, $R_1'$, $R_2'$ and $R_3$ are each, independently, hydrogen or $(C_{1-4})$alkyl, m is 1, $R_4$ and $R_5$ are each, independently, hydrogen, halogen, $(C_{1-4})$alkyl, $(C_{1-4})$alkoxy, $(C_{2-4})$acyl or trifluoromethyl and X is —CH$_2$— and n is 0, 1, 2 or 3, or X is —CO— and n is 1, 2 or 3, or X is —O— and n is 2 or 3, and acid addition salts thereof.

Another group of compounds comprises compounds of formula I wherein one of A and B is N and the other CH, Z is a ring of formula II, $R_1$ and $R_2$ are each, independently, hydrogen or $(C_{1-4})$alkyl, $R_3$ is hydrogen, $R_4$ is hydrogen or halogen, $R_5$ is hydrogen, X is —CH$_2$— and n is 0 or 1 or X is —CO— and n is 3 or X is —O— and n is 3 or an acid addition salt thereof.

Another group of compounds comprises compounds of formula I wherein one of A and B is N and the other CH, Z is a ring of formula III, $R_1'$ and $R_2'$ are either the same and signify hydrogen or $(C_{1-4})$alkyl or $R_1'$ and $R_2'$ together signify tetramethylene, $R_3$ is hydrogen, m is 1, $R_4$ is halogen, $R_5$ is hydrogen, X is —CO— and n is 3 or X is —O— and n is 3, or an acid addition salt thereof.

In a first group of compounds A is CH, B is N and Z is a ring of formula II.

In a second group of compounds A is N, B is CH and Z is a ring of formula II.

In a third group of compounds A is CH, B is N and Z is a ring of formula III.

In a fourth group of compounds A is N, B is CH and Z is a ring of formula III.

In a fifth group of compounds $R_1$ is hydrogen.

In a sixth group of compounds $R_1$ is $(C_{1-6})$alkyl.

In a seventh group of compounds $R_1$ is $(C_{7-10})$phenylalkyl.

In a eighth group of compounds $R_2$ is hydrogen.

In a nineth group of compounds $R_2$ is $(C_{1-6})$alkyl.

In a tenth group of compounds $R_2$ is $(C_{7-10})$phenylalkyl.

In a eleventh group of compounds $R_3$ is hydrogen.

In a twelvth group of compounds $R_3$ is $(C_{1-4})$alkyl.

In a thirteenth group of compounds $R_1'$ and $R_2'$ are hydrogen.

In a fourteenth group of compounds $R_1'$ and $R_2'$ are $(C_{1-4})$alkyl.

In a fifteenth group of compounds m=1.

In a sixteenth group of compounds X is —CH$_2$—.

In a seventeenth group of compounds X is —CO—.

In a eighteenth group of compounds X is —O—.

In a nineteenth group of compounds $R_4$ is hydrogen.

In a twentieth group of compounds $R_4$ is halogen.

In a twenty-first group of compounds $R_5$ is hydrogen.

What we claim is:

1. A compound of formula I,

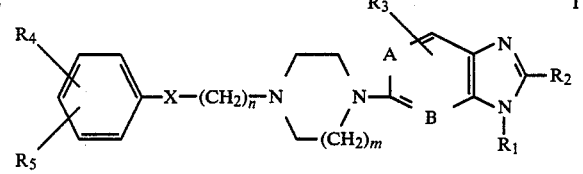

wherein one of A and B is N and the other CH, $R_1$ and $R_2$ are each, independently, hydrogen, $(C_{1-6})$-alkyl or $(C_{7-10})$phenylalkyl, optionally monosubstituted in the phenyl ring by halogen, $(C_{1-4})$alkyl or $(C_{1-4})$alkoxy, $R_3$ is hydrogen or $(C_{1-4})$alkyl, m is 1 or 2, $R_4$ and $R_5$ are each, independently, hydrogen, halogen, $(C_{1-4})$alkyl, $(C_{1-4})$alkoxy, $(C_{2-4})$acyl or trifluoromethyl, and X is —$CH_2$— and n is 0, 1 2 or 3, or X is —CO— and n is 1, 2 or 3, or X is —O— and n is 2 or 3, or a pharmaceutically acceptable acid addition salt thereof.

2. A compound of claim 1 wherein A is CH, B is N, $R_1$, $R_2$ and $R_3$ are each, independently hydrogen or $(C_{1-4})$alkyl, m is 1, $R_4$ and $R_5$ are each, independently, hydrogen, halogen $(C_{1-4})$alkyl, $(C_{1-4})$alkoxy, $(C_{2-4})$acyl or trifluoromethyl and X is —$CH_2$— and n is 0, 1, 2 or 3, or X is —CO— and n is 1, 2 or 3, or X is —O— and n is 2 or 3, or a pharmaceutically acceptable acid addition salt thereof.

3. A compound of claim 1 wherein A is N, B is CH, $R_1$, $R_2$ and $R_3$ are each, independently, hydrogen or $(C_{1-4})$alkyl, m is 1, $R_4$ and $R_5$ are each, independently, hydrogen, halogen, $(C_{1-4})$alkyl, $(C_{1-4})$alkoxy, $(C_{2-4})$acyl or trifluoromethyl and X is —$CH_2$— and n is 0, 1, 2 or 3, or X is —CO— and n is 1, 2 or 3, or X is —O— and n is 2 or 3, or a pharmaceutically acceptable acid addition salt thereof.

4. A compound of claim 1 which is 1-(4-fluorophenyl)-4-[4-(1H-imidazo[4,5-b]pyridin-5-yl)-1-piperazinyl]-1-butanone, or a pharmaceutically acceptable acid addition salt thereof.

5. A compound of claim 1 which is 1-(4-fluorophenyl)-4-[4-(2-ethyl-1H-imidazo[4,5-b]pyridin-5-yl)-1-piperazinyl]-1-butanone or a pharmaceutically acceptable acid addition salt thereof.

6. A pharmaceutical composition useful in treating schizophrenia, hypertension and cardiac disorders comprising a pharmaceutically acceptable carrier or diluent and a therapeutically effective amount of a compound of claim 1, or a pharmaceutically acceptable acid addition salt thereof.

* * * * *